United States Patent
Garber et al.

(10) Patent No.: US 9,066,815 B2
(45) Date of Patent: Jun. 30, 2015

(54) SPINAL IMPLANT WITH ATTACHMENT SYSTEM

(75) Inventors: Jason E. Garber, Las Vegas, NV (US); Christophe M. H. Geisert, Hüfingen (DE); Barbara D. Schweizer, Wurmlingen (DE); John Parry, Stamford, CT (US); John J. Viscogliosi, New York, NY (US)

(73) Assignee: CENTINEL SPINE, INC., New York, NY (US)

( * ) Notice: Subject to any disclaimer, the term of this patent is extended or adjusted under 35 U.S.C. 154(b) by 327 days.

(21) Appl. No.: 12/941,289

(22) Filed: Nov. 8, 2010

(65) Prior Publication Data
US 2011/0166658 A1 Jul. 7, 2011

Related U.S. Application Data

(60) Provisional application No. 61/259,391, filed on Nov. 9, 2009.

(51) Int. Cl.
*A61F 2/44* (2006.01)
*A61B 17/80* (2006.01)
(Continued)

(52) U.S. Cl.
CPC ........... *A61F 2/4465* (2013.01); *A61B 17/8038* (2013.01); *A61B 17/8042* (2013.01); *A61F 2002/2817* (2013.01);
(Continued)

(58) Field of Classification Search
CPC ......... A61F 2/442; A61F 2/44; A61F 2/4455; A61F 2220/0025; A61F 2220/0033; A61F 2220/0041; A61F 2002/30517

USPC ........... 623/17.11–17.16; 606/300–304, 319, 606/289, 291, 295–296
See application file for complete search history.

(56) References Cited

U.S. PATENT DOCUMENTS 4,599,086 A * 7/1986 Doty ............................ 606/86 A
5,800,433 A * 9/1998 Benzel et al. .................. 606/250
(Continued)

FOREIGN PATENT DOCUMENTS

GB 2457673 A 8/2009
WO 03/070128 A1 8/2003
(Continued)

OTHER PUBLICATIONS

European Examination Report dated Oct. 17, 2014, European Application No. 10784371.6 filed Nov. 8, 2010, pp. 1-4.

*Primary Examiner* — Eduardo C Robert
*Assistant Examiner* — Jacqueline Johanas
(74) *Attorney, Agent, or Firm* — MH2 Technology Law Group, LLP

(57) ABSTRACT

The embodiments of the present disclosure relate to a spinal implant assembly having features to prevent or minimize fixation elements, such as screws, from being dislodged, or from backing out over time and with use. The spinal implant assembly may comprise an implantable body having first apertures for receiving fixation elements. A plate configured to nest against the posterior portion of the implantable body and comprising one or more second apertures can be provided. These second apertures permit access to the head portions of the fixation elements. One or more locking elements are then passed through the second apertures and engage the head portions of the fixation elements. In addition, the plate may comprise an adjustable arm to allow the plate to be used with implantable bodies of different size.

20 Claims, 17 Drawing Sheets

(51) Int. Cl.
    *A61F 2/28*      (2006.01)
    *A61F 2/30*      (2006.01)

(52) U.S. Cl.
    CPC ............... *A61F 2002/2835* (2013.01); *A61F 2002/30056* (2013.01); *A61F 2002/30062* (2013.01); *A61F 2002/3008* (2013.01); *A61F 2002/30266* (2013.01); *A61F 2002/30367* (2013.01); *A61F 2002/30373* (2013.01); *A61F 2002/30492* (2013.01); *A61F 2002/30517* (2013.01); *A61F 2002/30538* (2013.01); *A61F 2002/30553* (2013.01); *A61F 2002/30578* (2013.01); *A61F 2002/30593* (2013.01); *A61F 2002/30785* (2013.01); *A61F 2002/30787* (2013.01); *A61F 2002/30794* (2013.01); *A61F 2002/30841* (2013.01); *A61F 2002/30878* (2013.01); *A61F 2210/0004* (2013.01); *A61F 2220/0025* (2013.01); *A61F 2220/0033* (2013.01); *A61F 2230/0082* (2013.01); *A61F 2250/0006* (2013.01); *A61F 2250/0008* (2013.01); *A61F 2250/0032* (2013.01); *A61F 2250/0098* (2013.01); *A61F 2310/00017* (2013.01); *A61F 2310/00023* (2013.01)

(56) References Cited

U.S. PATENT DOCUMENTS

| | | | | |
|---|---|---|---|---|
| 5,888,223 A | * | 3/1999 | Bray, Jr. | 623/17.16 |
| 5,980,522 A | * | 11/1999 | Koros et al. | 623/17.11 |
| 6,206,922 B1 | * | 3/2001 | Zdeblick et al. | 623/17.11 |
| 6,235,059 B1 | * | 5/2001 | Benezech et al. | 623/17.16 |
| 6,440,170 B1 | * | 8/2002 | Jackson | 623/17.16 |
| 6,471,724 B2 | * | 10/2002 | Zdeblick et al. | 623/17.16 |
| 6,576,017 B2 | * | 6/2003 | Foley et al. | 623/17.16 |
| 6,773,460 B2 | * | 8/2004 | Jackson | 623/17.15 |
| 6,926,737 B2 | * | 8/2005 | Jackson | 623/17.16 |
| 6,984,234 B2 | * | 1/2006 | Bray | 606/279 |
| 7,862,616 B2 | * | 1/2011 | Lechmann et al. | 623/17.11 |
| 7,985,258 B2 | * | 7/2011 | Zdeblick et al. | 623/17.16 |
| 8,187,329 B2 | * | 5/2012 | Theofilos | 623/17.11 |
| 8,328,872 B2 | * | 12/2012 | Duffield et al. | 623/17.16 |
| 2001/0005796 A1 | * | 6/2001 | Zdeblick et al. | 623/17.11 |
| 2004/0210314 A1 | * | 10/2004 | Michelson | 623/17.16 |
| 2006/0085071 A1 | * | 4/2006 | Lechmann et al. | 623/17.11 |
| 2007/0250167 A1 | * | 10/2007 | Bray et al. | 623/17.11 |
| 2008/0249625 A1 | | 10/2008 | Waugh et al. | |
| 2009/0088849 A1 | | 4/2009 | Armstrong et al. | |
| 2009/0192613 A1 | | 7/2009 | Wing et al. | |
| 2009/0210062 A1 | * | 8/2009 | Thalgott et al. | 623/17.16 |
| 2010/0057206 A1 | * | 3/2010 | Duffield et al. | 623/17.16 |
| 2010/0145460 A1 | * | 6/2010 | McDonough et al. | 623/17.16 |
| 2013/0317618 A1 | * | 11/2013 | Gause et al. | 623/17.16 |
| 2014/0277495 A1 | * | 9/2014 | Muhanna | 623/17.16 |
| 2014/0336768 A1 | * | 11/2014 | Blain | 623/17.16 |

FOREIGN PATENT DOCUMENTS

| | | |
|---|---|---|
| WO | 2004/069106 A1 | 8/2004 |
| WO | 2010/028095 A1 | 3/2010 |

* cited by examiner

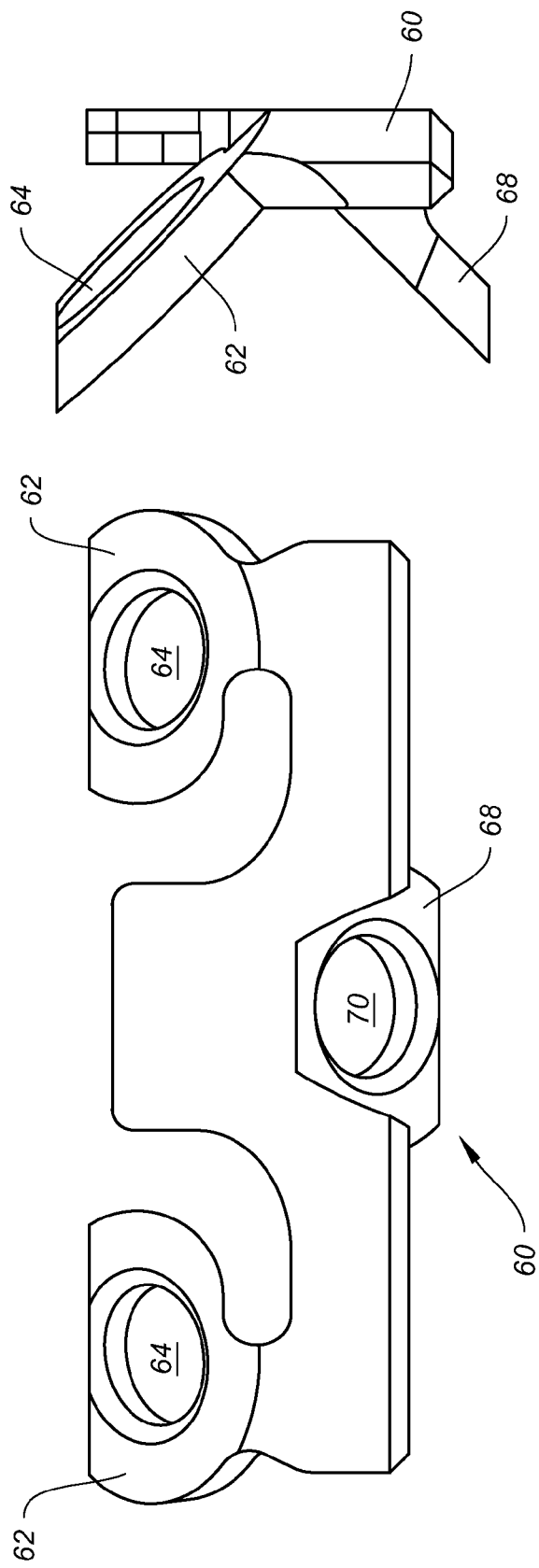

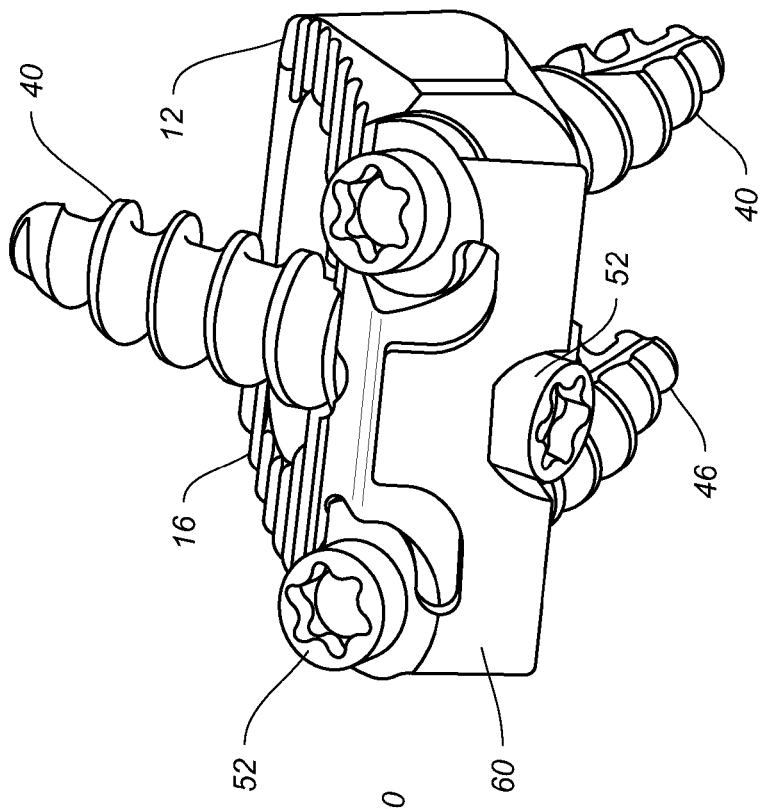
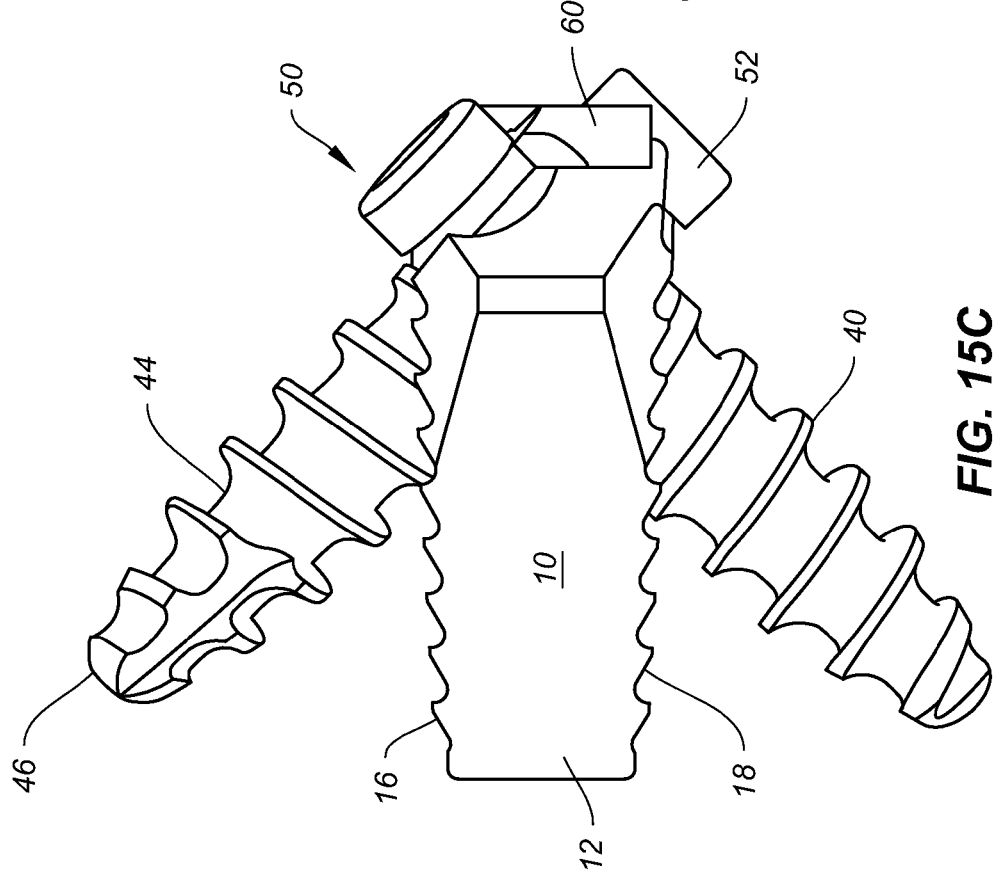
FIG. 15D
FIG. 15C

SPINAL IMPLANT WITH ATTACHMENT SYSTEM

CROSS-REFERENCE TO RELATED APPLICATIONS

This application claims priority to U.S. Provisional No. 61/259,391, filed Nov. 9, 2009, and entitled "SPINAL IMPLANT WITH ATTACHMENT SYSTEM," which is herein incorporated by reference in its entirety.

FIELD

The present disclosure relates to orthopedic implants, and more particularly, to spinal implants that facilitate fusion of bone segments and associated methods.

BACKGROUND

The integrity of the spine, including its subcomponents like the vertebral bodies and intervertebral discs that are well known structural body parts forming the spine, are key to a patient's health. These parts may become crushed or damaged as a result of trauma or injury, or damaged by disease (e.g., by tumor, auto-immune disease) or as a result of wear over time or degeneration caused by the normal aging process.

In many instances, one or more damaged structural body parts can be repaired or replaced with a prosthesis or implant. For example, specific to the spine, one method of repair is to remove the damaged vertebra (in whole or in part) and/or the damaged disc (in whole or in part) and replace it with an implant or prosthesis. In some cases, it is necessary to stabilize a weakened or damaged spinal region by reducing or inhibiting mobility in the area to avoid further progression of the damage and/or to reduce or alleviate pain caused by the damage or injury. In other cases, it is desirable to join together the damaged vertebrae and/or induce healing of the vertebrae. Accordingly, an implant or prosthesis may be configured to facilitate fusion between two adjacent vertebrae. The implant or prosthesis may be placed without attachment means or fastened in position between adjacent structural body parts (e.g., adjacent vertebral bodies).

Typically, an implant or prosthesis is secured directly to a bone structure by mechanical or biological means. One manner of spine repair involves attaching a fusion implant or prosthesis to adjacent vertebral bodies using a fixation element, such as a screw. Most implants and their attachment means are configured to provide an immediate, rigid fixation of the implant to the implantation site. Unfortunately, after implantation the implants tend to subside, or settle, into the surrounding environment as the patient's weight is exerted upon the implant. In some cases, this subsidence may cause the rigidly fixed attachment means to either loosen, dislodge or potentially damage one or more of the vertebral bodies. Furthermore, after insertion into the vertebral body, the fixation element or fixation system may work itself loose and/or back out, i.e., withdraw from the vertebral body. The consequence of back out or loosening includes improper or incomplete fusion, loss of stability, potential risk to the patient, and a separate costly and often painful revision surgery.

It is therefore desirable to provide a spinal fusion implant that avoids the problem of screw loosening or back out over time and with use. In addition, it is desirable to provide an implant and associated fixation elements that can account for subsidence that occurs with the implant subsequent to implantation while also providing rigid fixation.

Although the following discussion focuses on spinal implants or prostheses, it will be appreciated that many of the principles may equally be applied to other structural body parts within a human or animal body.

SUMMARY

The present disclosure describes a spinal implant assembly with an attachment system and one or more fixation elements, such as bone screws. In one embodiment, the attachment system securing the implant to adjacent bone tissue may be configured to prevent or minimize the screws from being dislodged, or from backing out over time and with use.

In one exemplary embodiment, a spinal implant assembly is provided. The assembly comprises a spinal implant having an upper surface, a lower surface, an anterior portion, a posterior portion and one or more apertures within the posterior portion for receiving at least one fixation element. The assembly further comprises a plate configured to nest against the posterior portion of the implant, the plate including one or more apertures for receiving at least one fixation element. Further, at least one locking element for securing the fixation element to the plate is provided. The locking element may comprise a pin, cap or plug, for example.

In another embodiment, a spinal implant assembly comprises an implantable body, a plate, and at least one locking element. The implantable body comprises an upper surface, a lower surface, an anterior portion, and a posterior portion. The implantable body can be configured for midline insertion between vertebral bodies of a patient's spine. The implantable body may also comprise one or more first apertures within the posterior portion of the implantable body for receiving at least one fixation element. The plate is configured to nest against the posterior portion of the implantable body and comprises one or more second apertures permitting access to a head portion of the at least one fixation element. The at least one locking element is shaped to pass through the at least one or more second apertures and secure the plate to the at least one fixation element based on engaging the head portion of the at least one fixation element.

In yet another embodiment, a method of treating a patient's spine comprises accessing at least a portion of a patient's spine via a posterior approach. An implantable body is inserted between vertebral bodies of the patient's spine, wherein the body comprises an upper surface, a lower surface, an anterior portion, a posterior portion, one or more first apertures within the posterior portion of the body for receiving a set fixation elements. The implantable body is attached with the set of elements to the vertebral bodies. A plate is placed onto the implantable body based on aligning one or more second apertures over head portions of the set of fixation elements. At least one locking element is then inserted through the one or more second apertures into the head portions of the set of fixation elements.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 4A illustrates a top-down view of the locking plate of the attachment system of FIG. 1.

FIG. 4B illustrates a side view of the locking plate of FIG. 4A.

FIGS. 15A-15D illustrate the method of assembling a spinal implant with an attachment system of the present disclosure.

DESCRIPTION OF THE EMBODIMENTS

Figure 1:
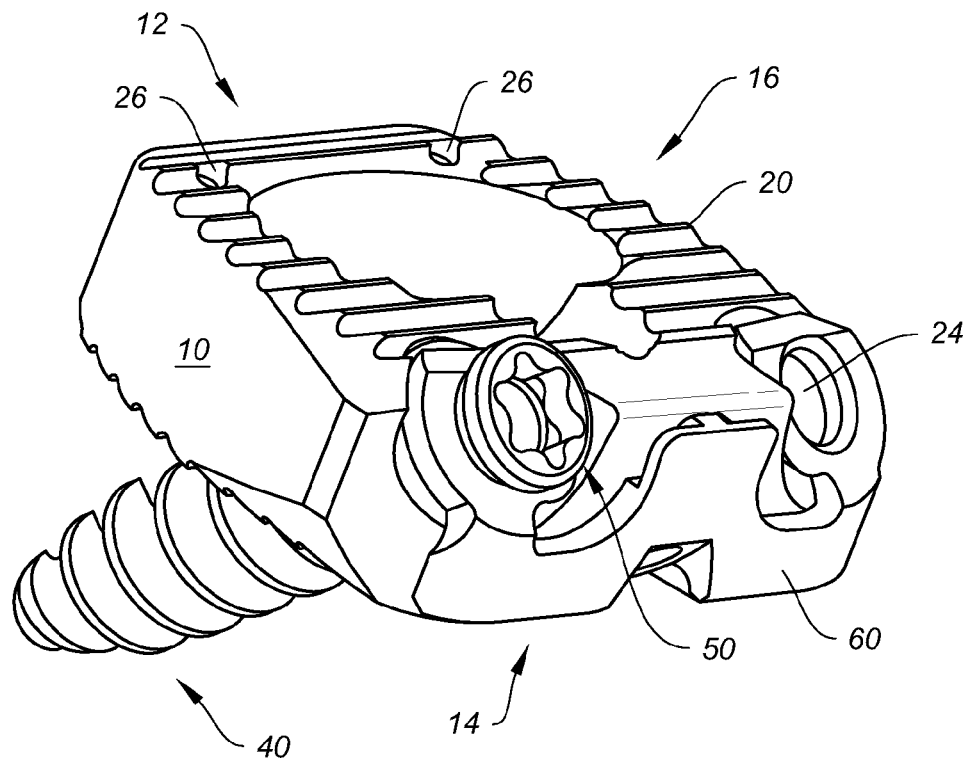
FIG. 1 illustrates a perspective view of a spinal implant with an attachment system of the present disclosure.

Referring now to FIG. 1, a spinal implant 10 with an attachment system 30 of the present disclosure is shown. The spinal implant 10 may be employed in the cervical region of the spine, in a manner similar to the one described for the cervical implant of U.S. patent application Ser. No. 11/938, 476 filed Nov. 12, 2007, entitled "Orthopaedic Implants and Prostheses," which is herein incorporated by reference in its entirety. Although the spinal implant 10 shown herein is configured for use in the cervical region, it is understood that the spinal implant 10 is not limited to a cervical application, and may be used in a different region of the spine as well, such as the lumbar or thoracic regions, so long as it is appropriately sized and configured, and the surgical approach takes into account this specific design.

The spinal implant 10 may include anterior and posterior portions 12, 14 and upper and lower surfaces 16, 18 profiled to correspond with the profile of any bone material to which they are to be secured. As shown, the upper and lower surfaces 16, 18 may further include surface enhancements, such as, teeth 20 to enhance bone attachment. In one embodiment, the teeth 20 may be formed at about a 30 degree angle with respect to the upper or lower surfaces 16, 18 of the implant 10. In other embodiments, the teeth 20 can have an angle between about 25 to about 35 degrees. It is understood, however, that alternative surface modifications such as surface roughenings, barbs, spikes, bumps, etc. may also be employed. In one embodiment, the spinal implant 10 defines a generally wedge shaped structure. The spinal implant 10, however, may have other shapes depending on the desired implantation site.

The spinal implant 10 and its components may be formed of any suitable medical grade material, such as biocompatible metals like stainless steel, titanium, titanium alloys, etc. or a medical grade plastic such as polyetheretherketone (PEEK) or another radiolucent material, ultra high molecular weight polyethylene (UHMWPE), etc. If so desired, the implant 10 may also be formed of a bioresorbable material. The bioresorbable material may preferably be osteoconductive or osteoinductive (or both).

As shown, the spinal implant 10 may include a central opening or lumen 22 extending between the upper and lower surfaces 16, 18 to facilitate bony ingrowth or fusion between adjacent bone segments, such as vertebral bodies. If so desired, the opening 22 may be used to receive and hold bone graft material.

The spinal implant 10 may include holes 24 for placement of fixation screws therethrough to secure the spinal implant 10 to adjacent bone tissue. In the embodiment shown, the implant 10 includes three holes 24, one hole being centrally located (i.e., along the center line), and two laterally located (i.e., aside the center line). One skilled in the art will appreciate that the implant 10 may comprise any number of holes in any location on the implant 10. For instance, a two-hole version of the spinal implant 10 may be envisioned. Optionally, the implant 10 may comprise holes 26 for receiving features like a radiologic marker or other imaging marker.

The holes 24 provide a path through which securing means (e.g., fixation elements such as bone screws) may be inserted so as to secure the implant 10 to respective superior and inferior vertebral bodies (not shown). The holes 24 may be configured to accommodate a variety of securing means, such as screws, pins, staples, or any other suitable fastening device.

The holes 24 of the spinal implant 10 may be configured to permit a predetermined amount of screw toggle (i.e., angular skew) and enable a lag effect when the fixation screw 40 is inserted and resides inside the hole or lumen 24. In other words, the holes 24 permit a certain degree of nutation by the screw 40 and thus the screws 40 may toggle from one position to one or more different positions, for instance, during subsidence. It also is believed that the predetermined screw toggle (permitted by the clearance between the lumen, or hole 24 and the screw 40) promotes locking of the screw 40 to the implant 10 after subsidence subsequent to implantation. Screw toggle may also be permitted based on the contours of the head of fixation screws 40, the shape of holes 64 and 70 of fixation plate 60, and tolerances of the locking pins 50. In one embodiment, the predetermined amount of screw toggle may be about 3 to 8 degrees, or about 5 to 6 degrees. Alternatively, the holes 24 of implant 10 may be configured with little or no clearance to achieve rigid fixation.

As shown, the spinal implant 10 may be secured with an attachment system 30 comprising one or more fixation screws 40, locking pins 50, and a locking plate 60. The attachment system 30 generally acts as an anti-backout mechanism to prevent the fixation screws 40 from loosening or rotating and backing out over time and with use.

The fixation screws 40 may be self-tapping and self-drilling and may be of a bone-screw-type, such as those well known to skilled artisans. In some embodiments, the head portion 42 of the fixation screws 40 may comprise a bored section 48 that can accommodate the locking pins 50. As also shown, the bored section 48 may be configured to allow nutation of the locking pins 50, and thus, in addition to toggling by fixations screws 40, locking pins 50 may also be permitted to have a certain degree toggling. The amount of respective nutation allowed for the fixations screws 40 and locking pins 50 may be the same or different depending upon the desired freedom of toggling. For example, fixation screws 40 may be permitted a larger degree of nutation, while locking pins 50 may be permitted a smaller degree of nutation relative to the fixation screws. Of course, in some instances, locking pins 50 may be permitted the larger amount of nutation relative to the fixation screws 40. This feature may be useful to allow the implant 10 to settle in situ, for example, during subsidence. In some embodiments, the bored section 48 may be a specific depth corresponding to a length of the locking pins 50, for example, to prevent over insertion.

The locking pins 50 secure the locking plate 60 onto fixation screws 40. In some embodiments, the locking pins 50 are configured for insertion into the head portion 42 of fixation screws 40. As shown, in some embodiments, the locking pins 50 may comprise a head 52 with a tool opening, such as a contoured bore 58, for receiving an inserter tool (not shown). The locking pins 50 and alternative embodiments are further described with reference to FIG. 3.

The locking plate 60 forms a complementary fit with the spinal implant 10. As shown, the locking plate 60 may include holes 64, 70 that align with the screw holes on the implant 10. The holes 64, 70 may be sized appropriately to allow or restrict nutation of the locking pins 50. In addition, the holes 64, 70 may be configured to provide the same or different amounts of nutation. Thus, the implant 10 can provide a wide variety of toggling configurations depending on its desired usage.

Figure 2:
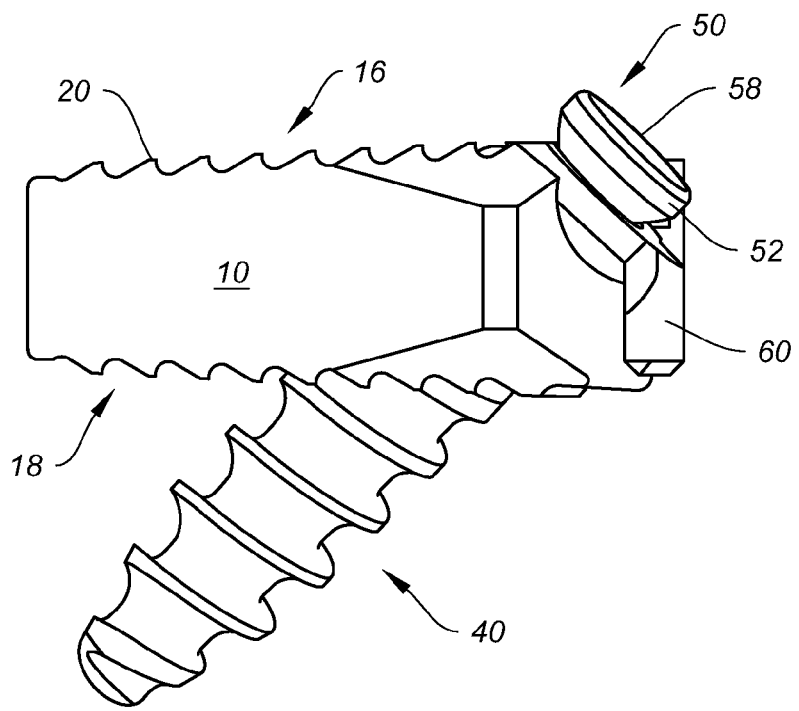
FIG. 2 illustrates a side view of the spinal implant with the attachment system of FIG. 1.

FIG. 2 illustrates a side view of the spinal implant with the attachment system 30 of FIG. 1. As shown, the locking pins 50 and fixation screws 40 may be substantially coaxial. As noted, however, one or both of locking pins 50 and fixation screws 40 may be configured with at least some amount of allowed nutation to provide toggle based on predetermined tolerances and clearances. In other embodiments, the locking pins 50 and fixation screws 40 may be configured with little or no tolerances in order to be mated rigidly together.

Figure 3:
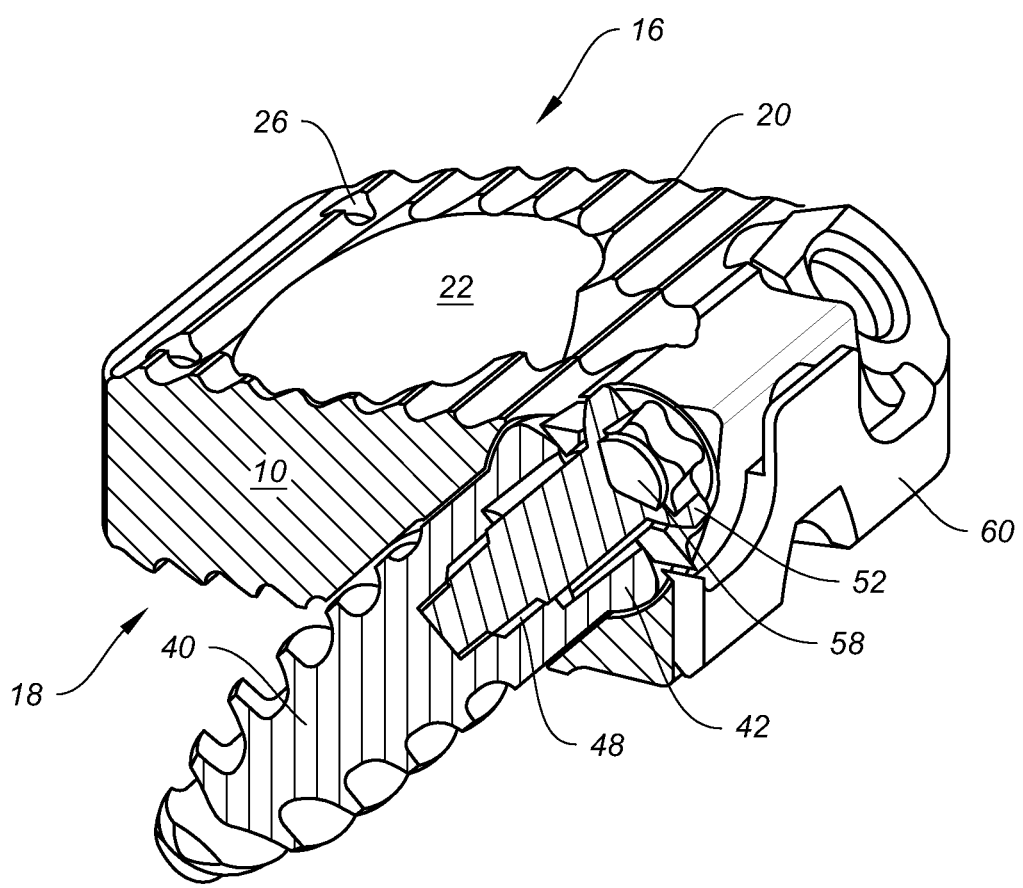
FIG. 3 illustrates a partial cutaway side view of the spinal implant with the attachment system of FIG. 1.

FIG. 3 illustrates a partial cutaway side view of the spinal implant with the attachment system of FIG. 1. As shown, the locking pins 50 may sit proud atop the locking plate 60. Alternatively, the locking pins 50 may sit flush against the locking plate 60, for example, to reduce the overall profile or thickness of the implant 10.

Referring now to FIGS. 4A and 4B, the locking plate 60 may comprise a plurality of arms. For example, in the embodiment shown, locking plate 60 may comprise lateral arms 62 and a central arm 68. Each arm provides a respective aperture 64 and 70 through which locking pins 50 extend into fixation screws 40. In particular, once appropriately placed on the posterior portion 14 of the implant 10, the apertures 64 and 70 are substantially aligned with the bored sections 48 of the fixation screws 40. As also shown, these apertures 64 and 70 may be countersunk.

Figure 6:
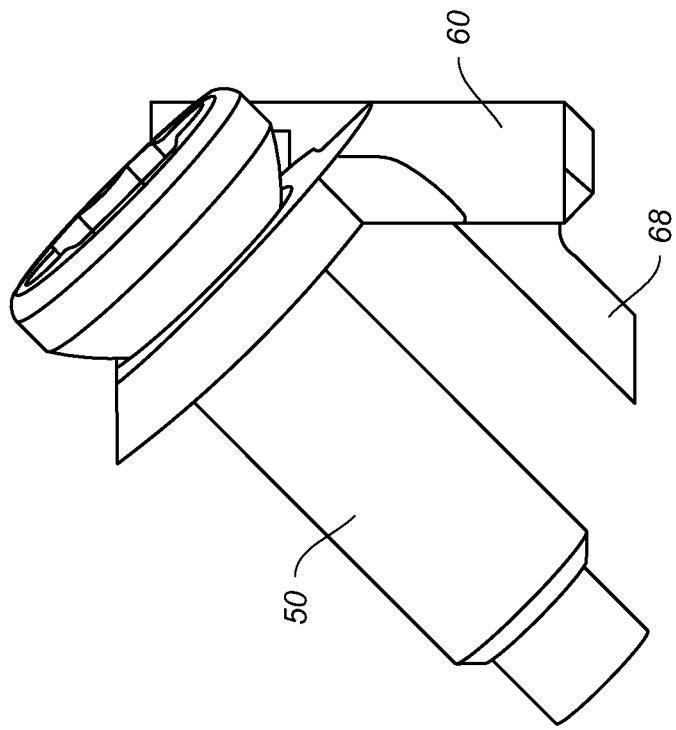
FIG. 6 illustrates a side view of the locking pin of the attachment system of FIG. 1.
Figure 5:
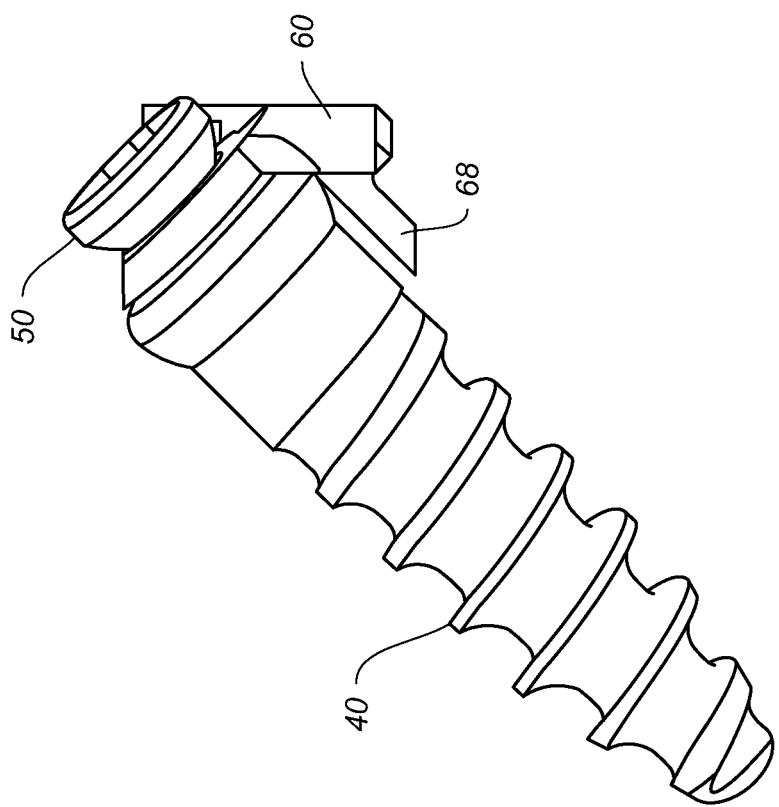
FIG. 5 illustrates a side view of the fixation screw system attached to the locking plate of FIG. 1.

FIGS. 5 and 6 illustrate the relationship of the locking pins 50 to the fixation screws 40 and to the locking plate 60, respectively. In particular, FIG. 5 shows locking pin 50 securing locking plate 60 to fixation screw 40. FIG. 6 illustrates an enlarged view of locking pin 50 extending through locking plate 60.

Figure 7A:
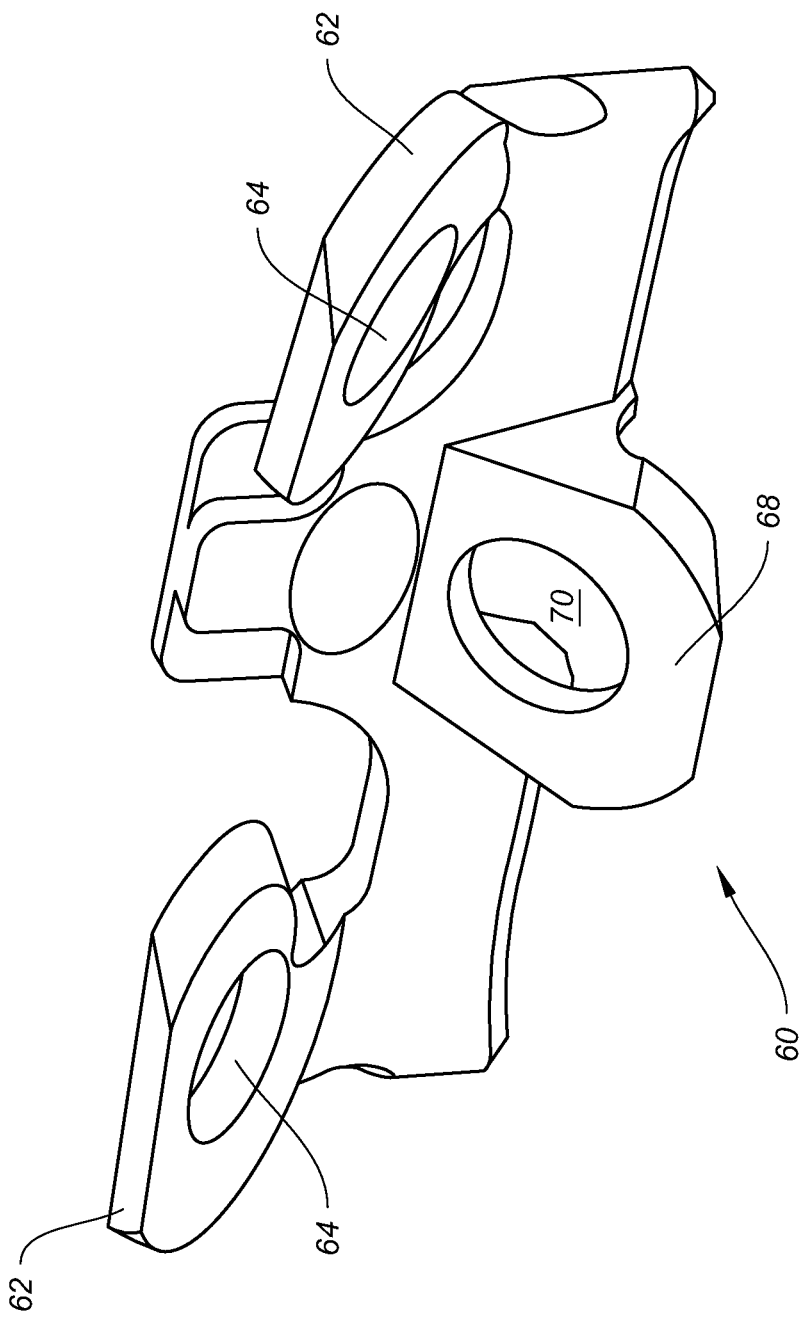
FIG. 7A illustrates a perspective rear view of the locking plate of FIG. 1.

FIG. 7A depicts a rear view of one embodiment of the locking plate 60. As shown in detail, the contours and angles of the locking plate are designed and sized so as to form a complementary fit to the posterior portion 14 of the spinal implant 10. It is contemplated that the locking plate 60 may be sized to provide a suitable overall thickness and weight of the finally assembled and implanted system.

Figure 7B:
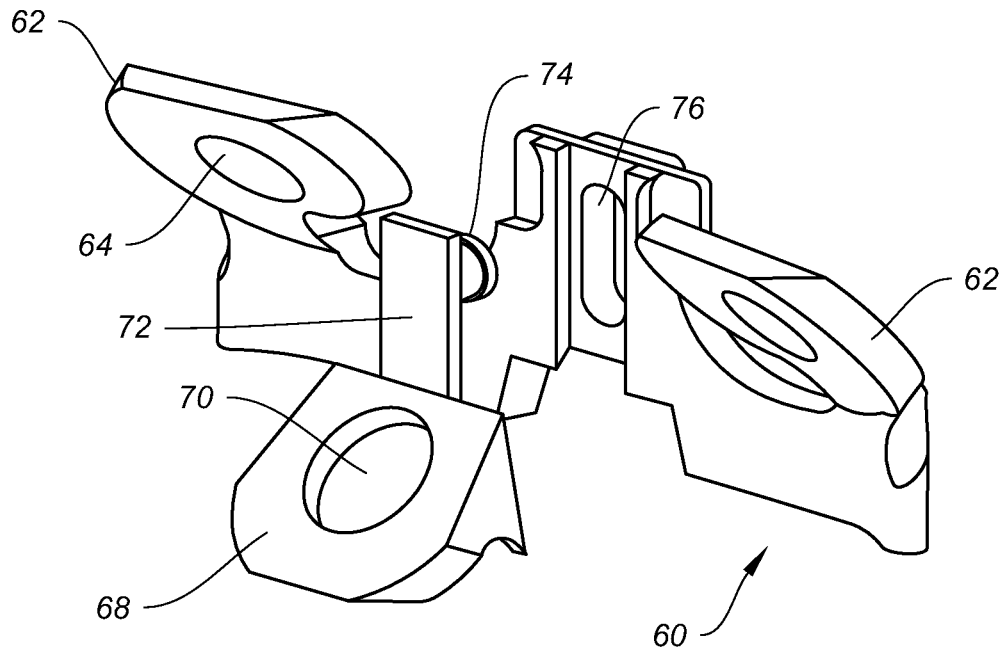
FIG. 7B illustrates an exploded view of a locking plate assembly of the present disclosure.
Figure 7C:
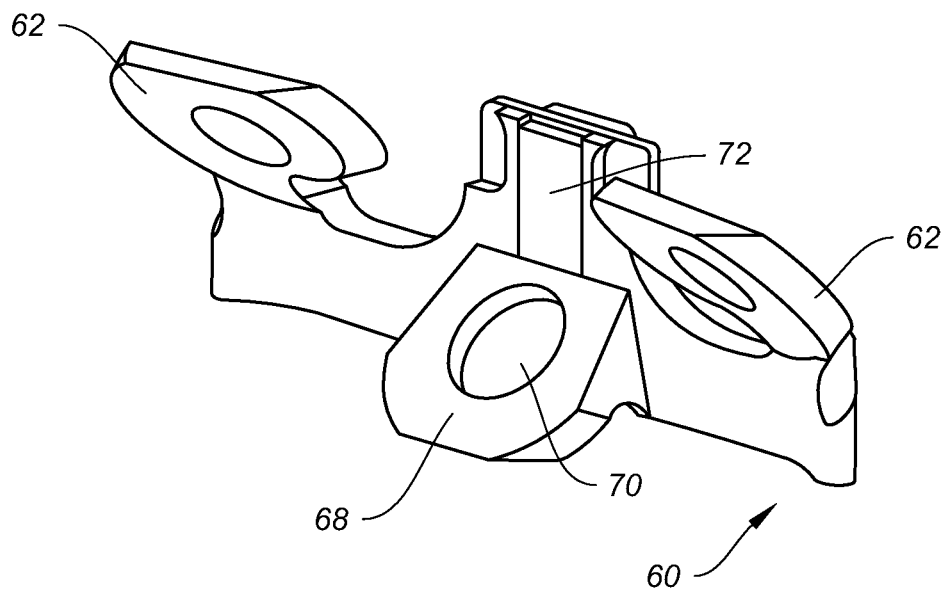
FIG. 7C illustrates the assembled locking plate assembly of FIG. 7B.
Figure 7D:
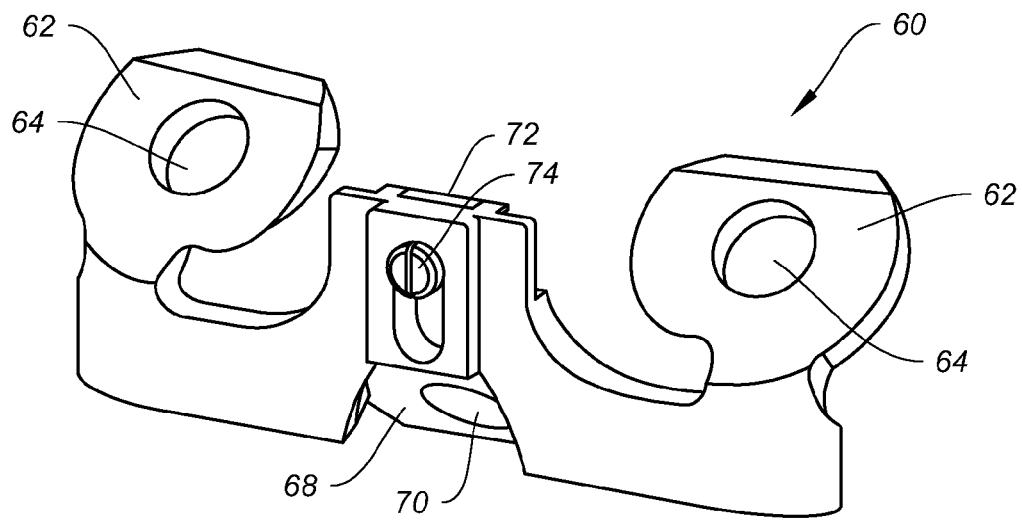
FIG. 7D illustrates a front view of the locking plate assembly of FIG. 7B in a first position.
Figure 7E:
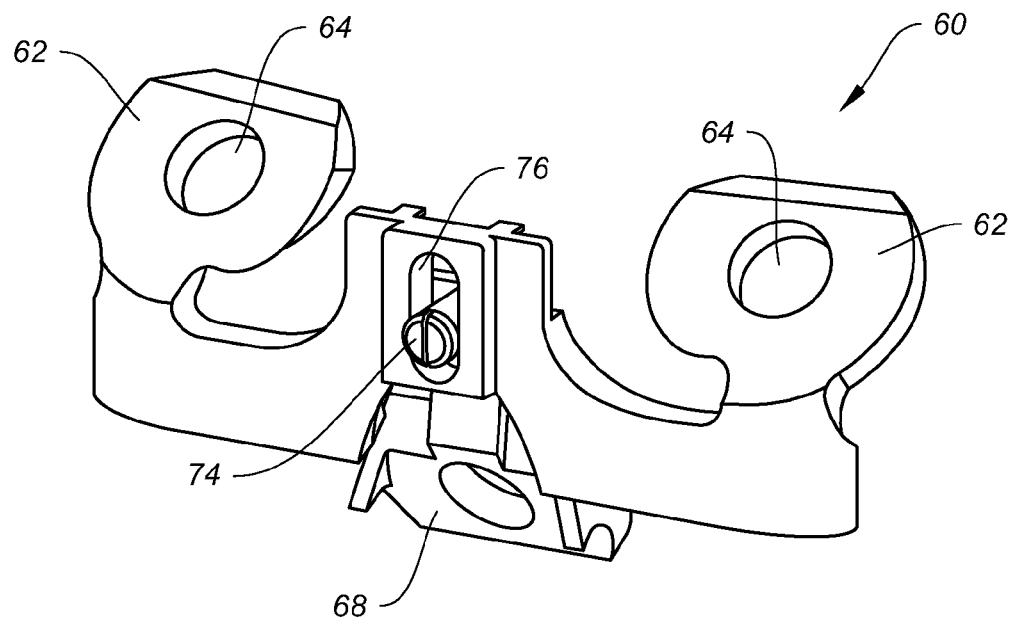
FIG. 7E illustrates a front view of the locking plate assembly of FIG. 7B in a second position.

FIGS. 7B-7D illustrate several views of an alternative embodiment of the locking plate 60 that allows it to accommodate a variety of implant sizes. For example, the central arm 68 may be adjustable, such as height adjustable, relative to the rest of locking plate 60. As shown, the central arm 68 may comprise a tab 72 and knob 74 that fits into a slot 76 provided on locking plate 60. In addition to this type of lock-and-key sliding mechanism, a variety of adjustable mechanisms may be implemented on the locking plate 60. In addition, these adjustable mechanisms may comprise a locking feature to fix the central arm 68 at a specific location and size.

Figure 8A:
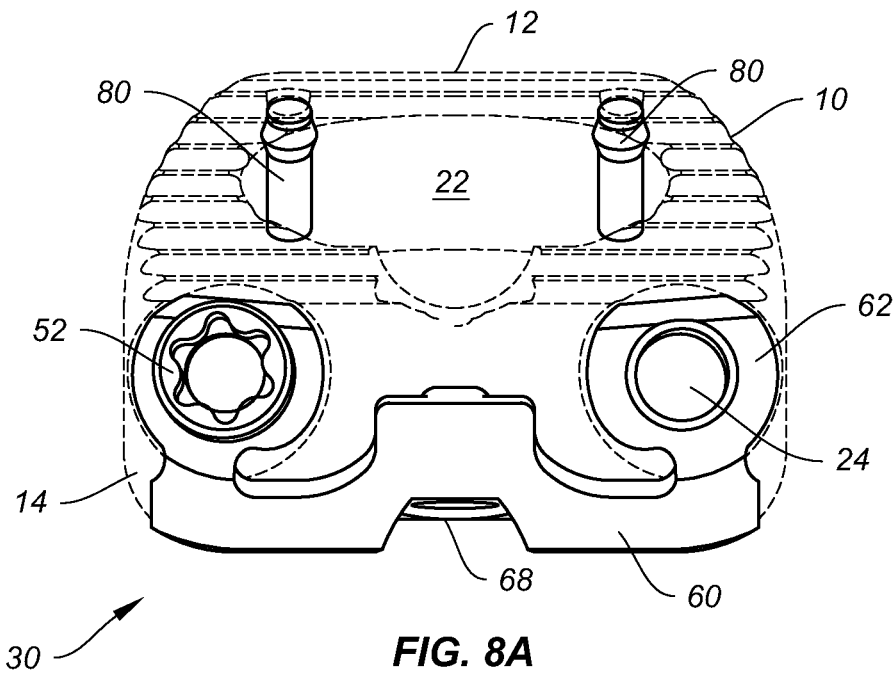
FIG. 8A illustrates a superior cutaway view of the spinal implant with attachment system of FIG. 1 and radiolucent markers.
Figure 8B:
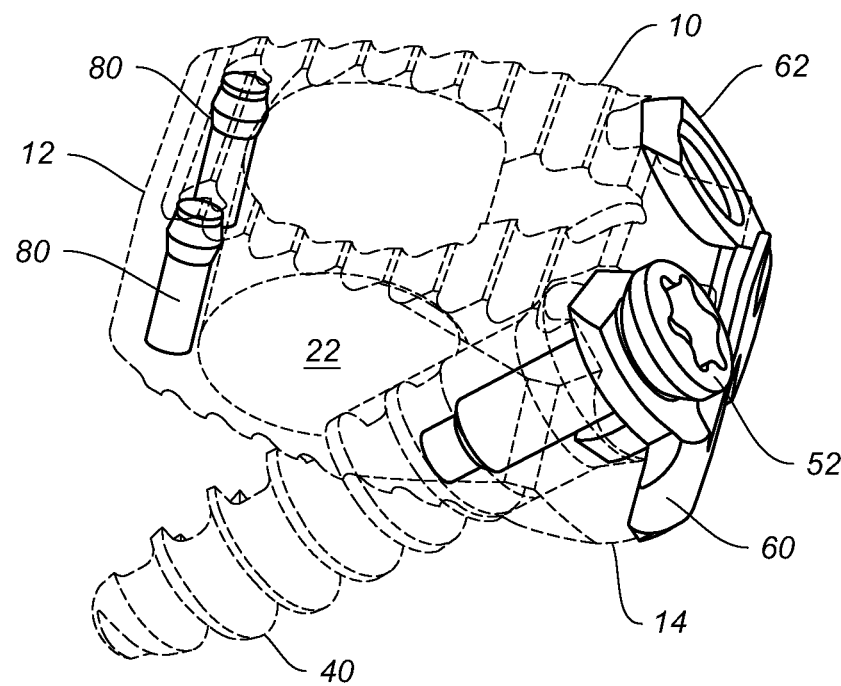
FIG. 8B illustrates a perspective cutaway side view of the spinal implant with attachment system of FIG. 8A.

FIGS. 8A and 8B show various cutaway views of the implant 10 with the attachment system 30. As also shown, the implant 10 may comprise other features, such as radiological markers 80 or imaging markers.

Figure 9:
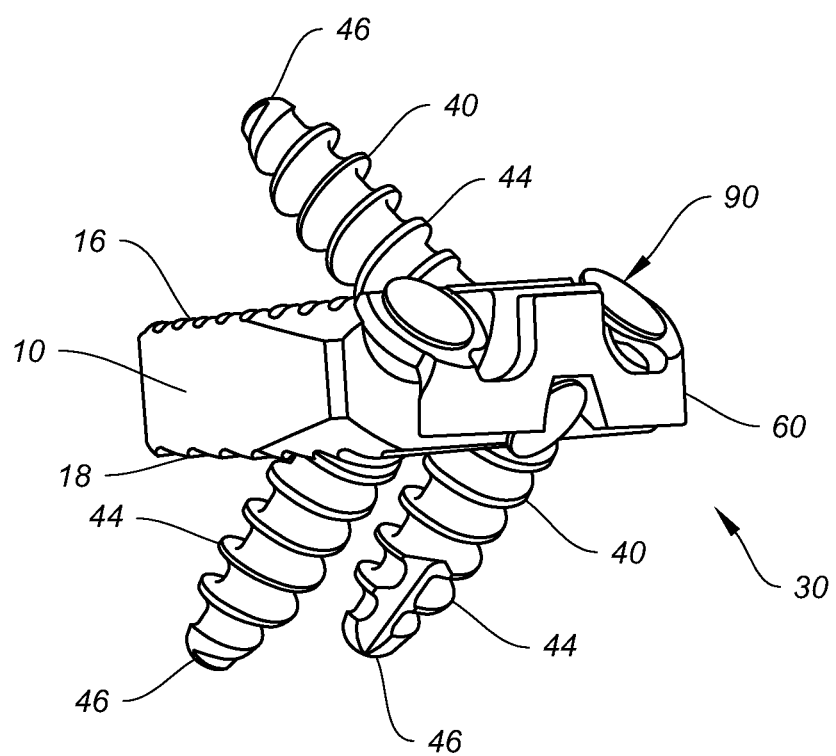
FIG. 9 illustrates a perspective view of another exemplary embodiment of a spinal implant with attachment system of the present disclosure.

FIG. 9 illustrates an alternative embodiment of the locking pins 50. As shown, the locking pins 50 may comprise locking caps 90 that are inserted into the bored section 48 of fixation screws 40. As shown, the locking caps 90 may comprise a closed top surface. This form of locking pin may be desirable to permit installation without the need for a tool, for example, using manual force to achieve a press fit or interference fit.

Figure 10A:
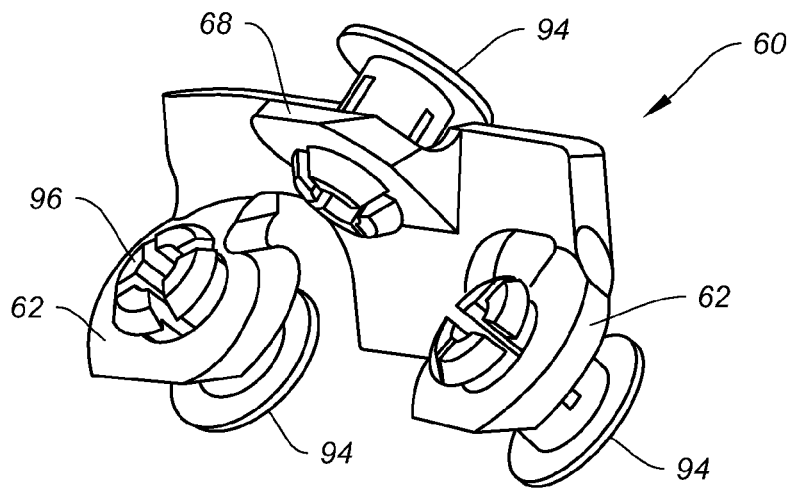
FIG. 10A illustrates a perspective rear view of the attachment system of FIG. 9.
Figure 10B:
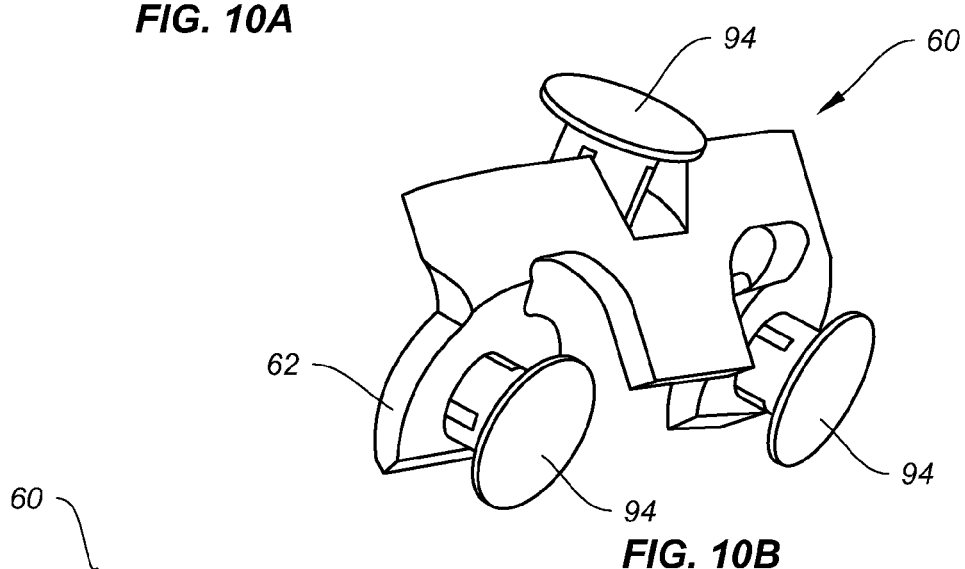
FIG. 10B illustrates a perspective front view of the attachment system of FIG. 10A.
Figure 10C:
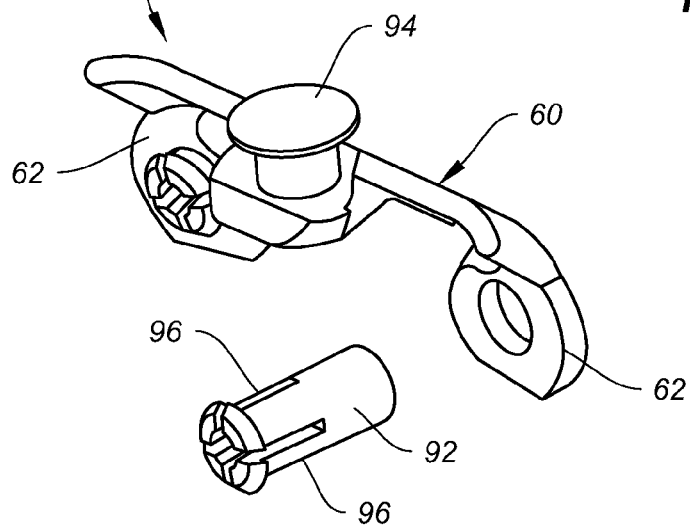
FIG. 10C illustrates an exploded view of the attachment system of FIG. 10A.

FIGS. 10A-10C illustrate another view of locking pins 50 as a locking plug 90. As shown, the locking pins 50 comprise an elongate body 92 having multiple legs or finger projections 96 extending from a head portion 94. The finger projections 96 can be configured to be flexible, enabling the surgeon or user to force the projections 96 through the screw holes 64 and 70 of locking plate 60 and into the bored section 48 of fixation screws 40 with some desired amount of external pressure. The terminal ends of the legs or finger projections 96 may then enlarge as they enter the bored section 48 of the fixation screw 40 to form a press fit or interference fit, so that the locking pins 50 are secured to the fixation screw 40 once it is inserted through the locking plate 60.

Figure 11A:
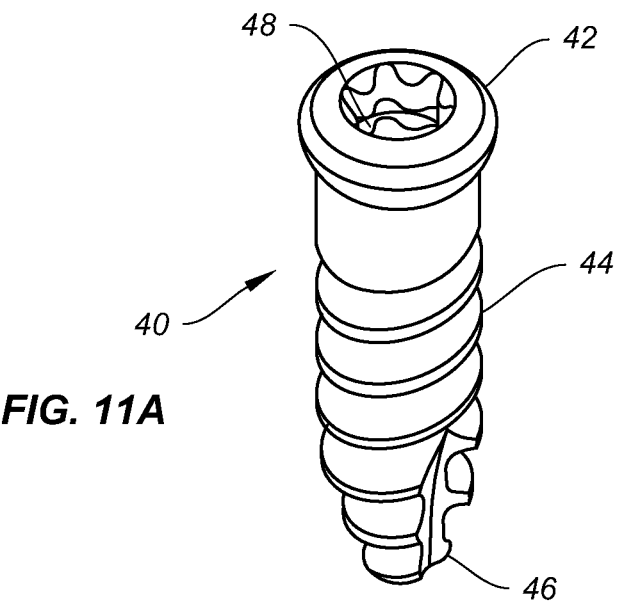
FIG. 11A illustrates a perspective view of a fixation screw of the attachment system of FIG. 9.
Figure 11B:
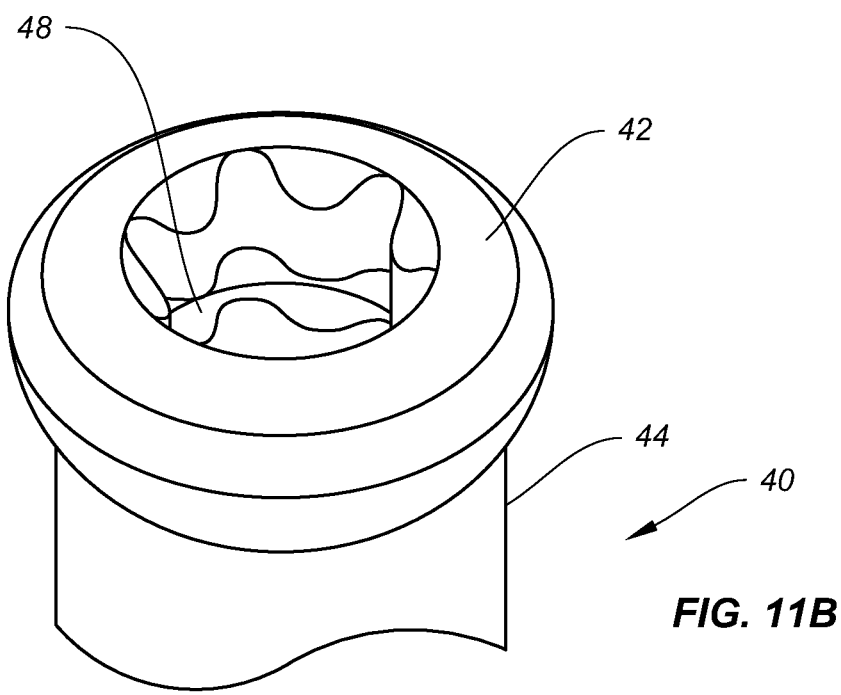
FIG. 11B illustrates an enlarged view of the fixation screw of FIG. 11B.

FIGS. 11A and 11B depict an embodiment of the fixation screws 40. As shown, a fixation screw 40 may have head portion 42, a threaded shaft 44, a self-drilling end 46, and bored section 48. As shown, the bored section 48 may be configured with a shape to receive a tool for insertion and shaped to receive the finger projections 96 of the locking pins 50 shown in FIGS. 10A-10C.

Figure 12A:
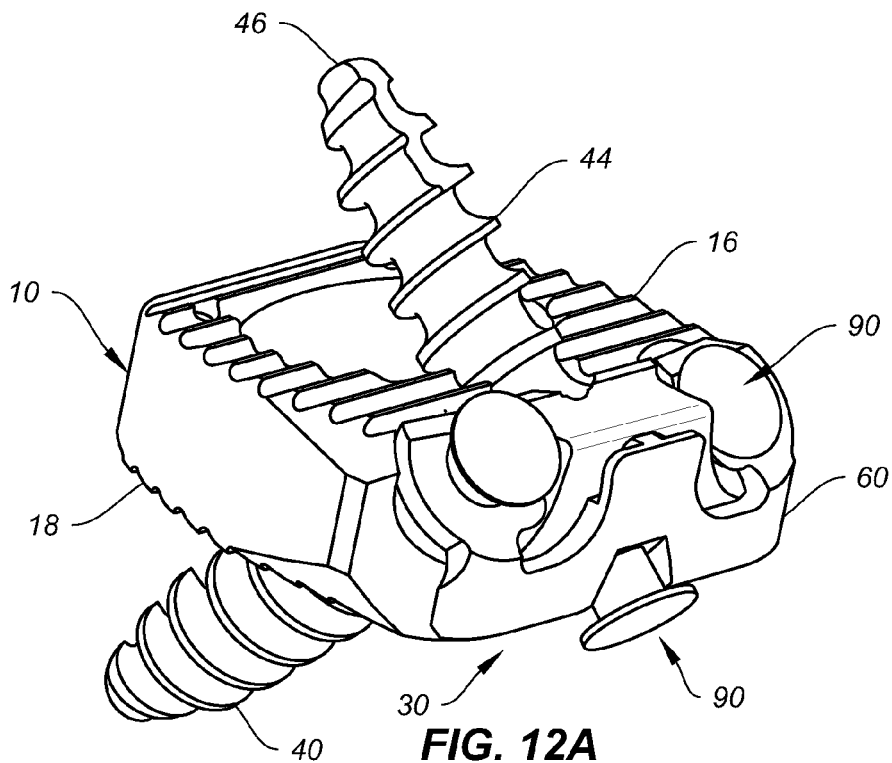
FIG. 12A illustrates a perspective view of a partially assembled spinal implant with attachment system of FIG. 9.
Figure 12B:
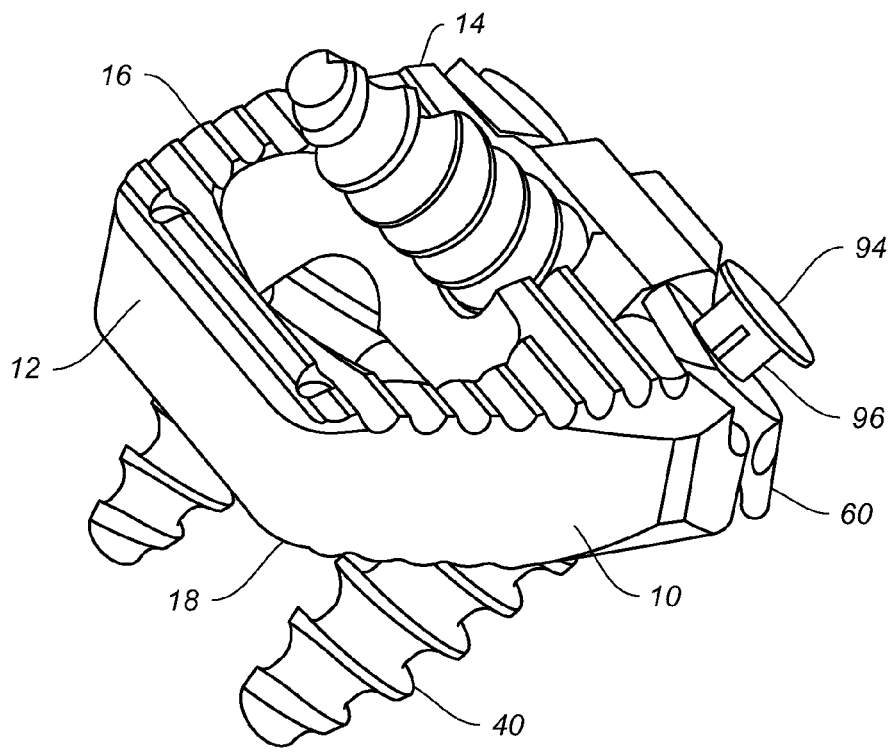
FIG. 12B illustrates another perspective view of the spinal implant with attachment system of FIG. 12A.

FIGS. 12A and 12B illustrate different perspective views of the spinal implant 10 and attachment system 30, partially assembled. As illustrated, the fixation screws 40 are first inserted through the spinal implant 10. The locking plate 60 can then be placed over the spinal implant 10 and fixation screws 40. As shown, the locking pins 50 are similar to those illustrated in FIGS. 10A-10C, and thus, are locking caps that can be pushed through the holes 64 and 70 of the locking plate 60 to secure the entire assembly and implant together.

Figure 13A:
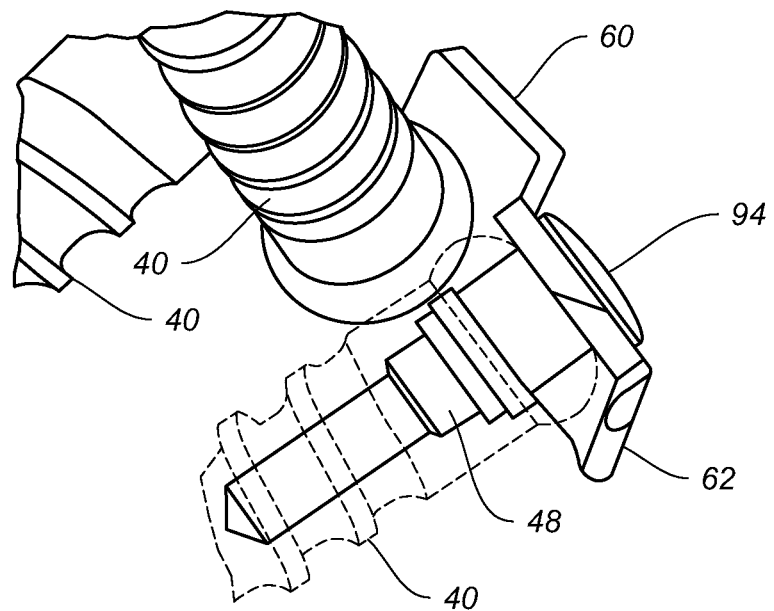
FIG. 13A illustrates a perspective view of the fixation screw and locking pin of the attachment system of FIG. 12A.
Figure 13B:
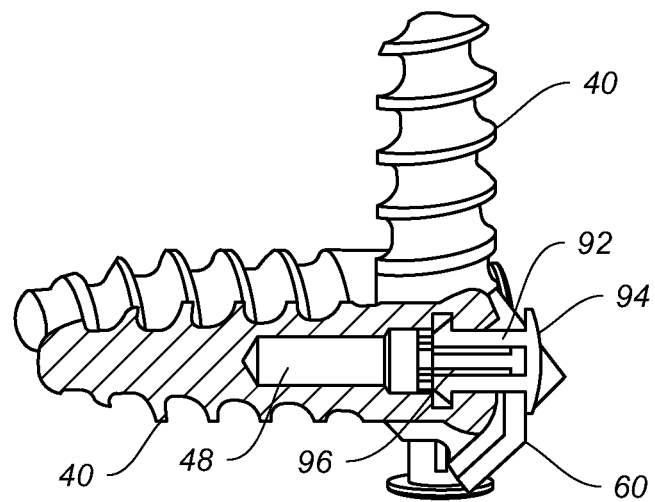
FIG. 13B illustrates a cutaway view of the fixation screw and locking pin of the attachment system of FIG. 13A.

FIG. 13A shows a partial cutaway view of a fixation screw 40 and an attached to locking cap 50, with the locking plate 60 in between. FIG. 13B shows another cutaway view of the same components.

Figure 14A:
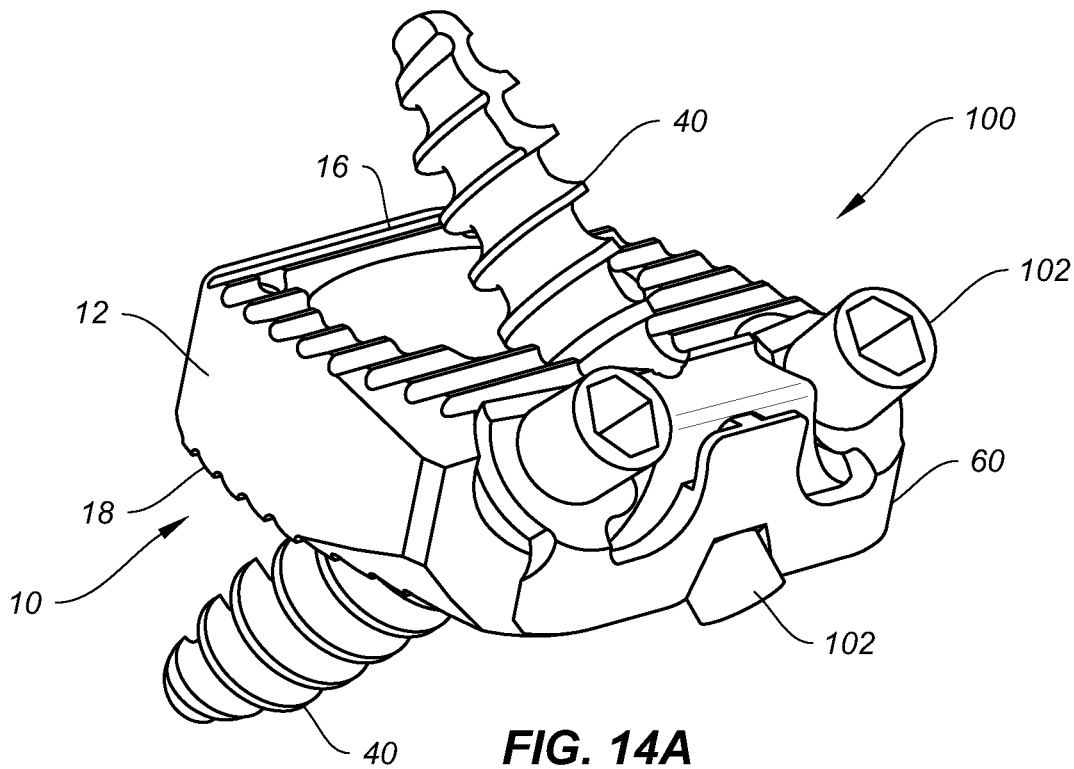
FIG. 14A illustrates a perspective view of yet another exemplary embodiment of a spinal implant with attachment system of the present disclosure.
Figure 14B:
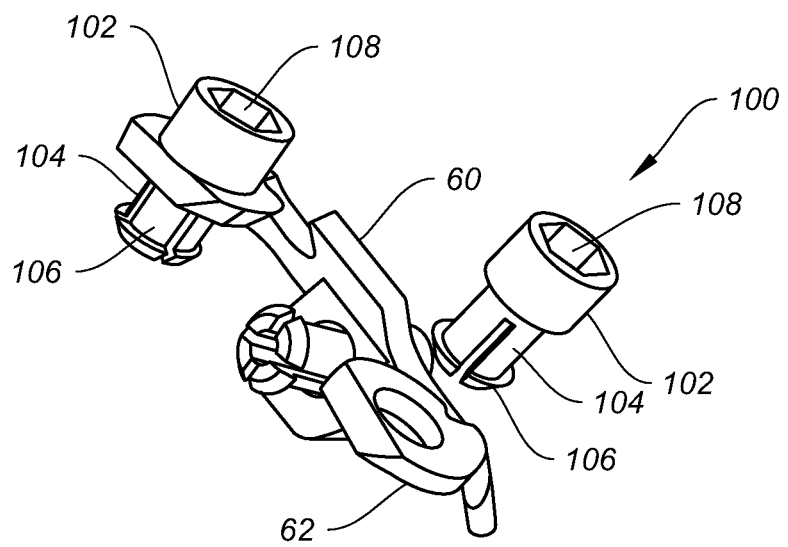
FIG. 14B illustrates an exploded view of the attachment system of FIG. 14A.

FIGS. 14A and 14B show yet another embodiment of a spinal implant and attachment system of the present disclosure. The spinal implant 10 and locking plate 60 may be similar to those described above. However, in this embodiment, the locking pins 50 comprise a locking plug 100. As shown, the locking plug 100 may comprise a head 102 and an elongate body 104 having legs or finger projections 106 extending from the head 102. In addition, the head 102 may comprise a cylindrical body with a center bore 108 shaped to mate with an insertion tool (not shown). In the embodiment shown, the bore 108 is shaped like a hexagon. However, it is understood that any shape or size may be used in the embodiments of the present disclosure.

Figure 15A:
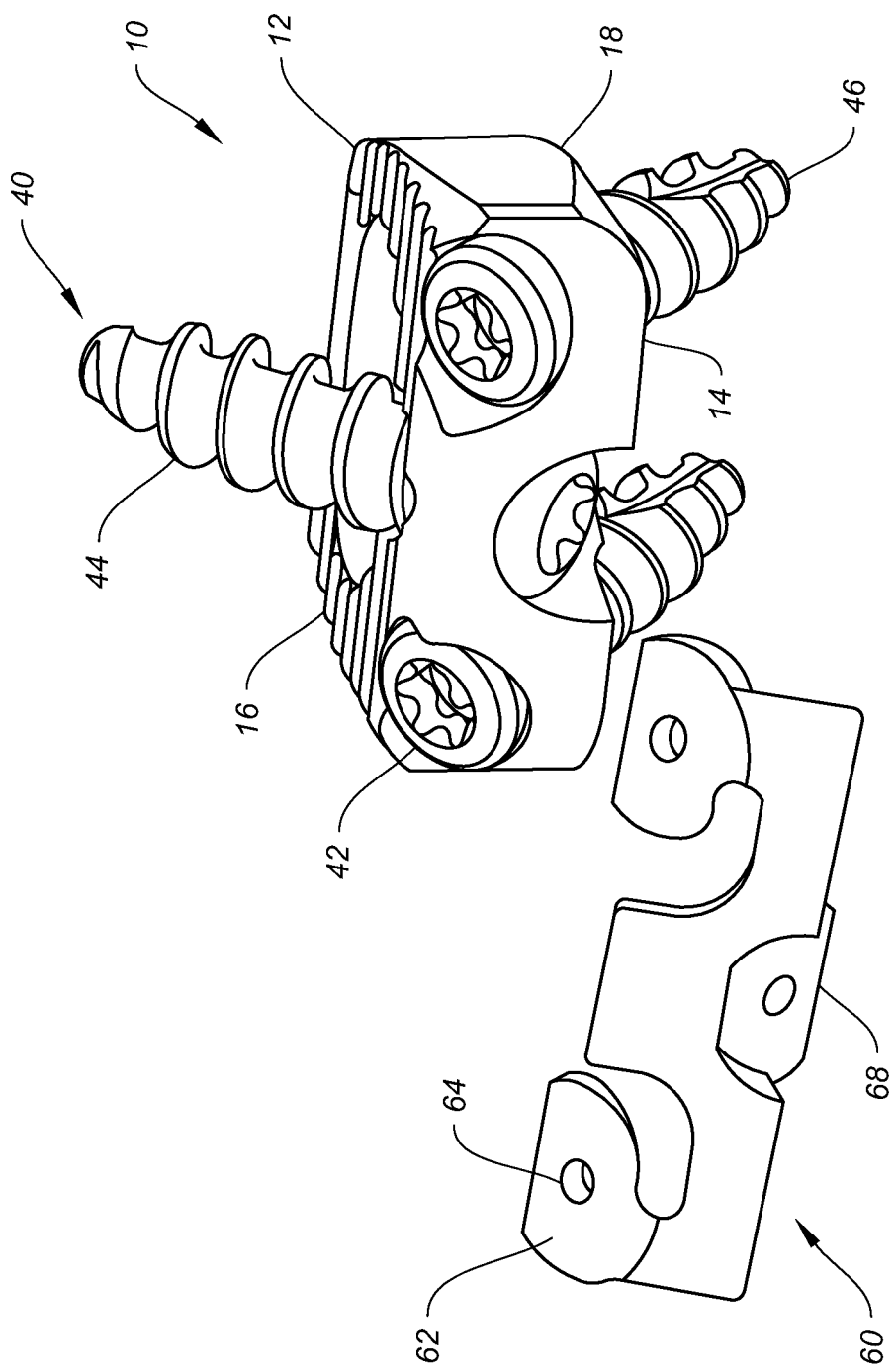
Figure 15B:
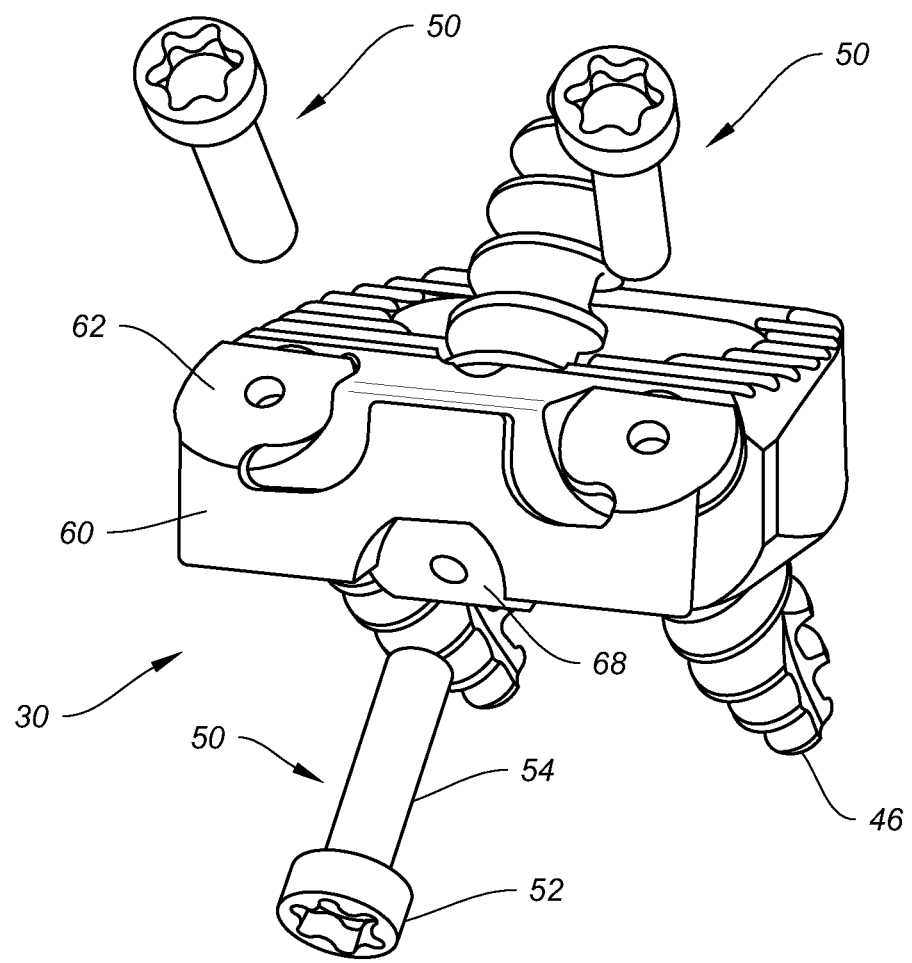

FIGS. 15A-15D conceptually depict a method of assembling the spinal implant and attachment system of the present disclosure. As shown in FIG. 15A, the spinal implant 10 is provided with fixation screws 40. The spinal implant 10 may be provided to the surgeon with the screws 40 pre-attached, or separately, as desired. After the surgeon places the implant 10 in the desired location, such as the cervical region of a patient's spine, the surgeon can tighten the screws 40 into the surrounding bone tissue, thereby securing the implant 10.

As noted, the implant 10 may be configured to permit a predetermined amount of screw toggle and enable a lag effect when the fixation screw 40 is inserted and resides inside the hole or lumen 24. Upon tightening, the lag effect may be observed whereby the implant 10 draws bone tissue towards itself, which may promote better fusion.

As further noted, the predetermined screw toggle promotes locking of the screw 40 to the implant 10 after subsidence subsequent to implantation. For example, after surgery, the patient's natural movement will result in settling and subsidence of bone tissue and the implant 10 in situ. It is believed that during this process, the weight exerted upon the implant 10 causes the fixation screws 40 to toggle and consequently lock against one or more surfaces of the holes 24 of the implant 10.

To ensure that the implant 10 stays in place over time and with use, the surgeon may then place the locking plate 60, such as the one shown in FIG. 15A onto the posterior portion 14 of the spinal implant 10.

Once the locking plate 60 has been placed onto the implant 10, the surgeon may then insert the locking pins 50 through holes 64 and 70 provided on the locking plate 60. As noted, these screw holes are configured to align with the bores 48 of the fixation screws 40. Although shown in FIG. 15B with a smooth outer elongate body 54, the locking pins 50 may have any variety of surface features. For example, it is contemplated the pins 50 may have threads, teeth, barbs, surface roughenings, etc. to assist in mating to their respective fixation screws 40. Where rigid fixation is desired (i.e., the attachment system does not provide toggle), the underside of the locking pins 50 may also include surfaces features as well in order to provide secure attachment between the locking pin 50 and the plate 60. Furthermore, in some embodiments, the locking pins 50 may be configured to splay and expand the diameter at least some portion of the head 42 of the fixation screws 40.

As shown in FIGS. 15C and 15D, the holes 64 and 70 of the locking plate may also be configured to facilitate the insertion of the locking pins at a specific angle for mating into the fixation screws 40. FIGS. 15C and 15D are provided to show various views of a fully assembled spinal implant 10 with attachment system.

Some practitioners prefer to allow some degree of movement between the implant and the adjacent vertebral body after implantation. In that case the locking pin 50 may be provided with contours on its underside that allow the pin 50 to nutate and toggle with respect to the contoured opening 64, 70 of the plate 60. This allowed nutation of the locking pin 50 may be in addition to or in replacement of toggling by fixation screws 40. Other practitioners may prefer a more rigid implant assembly that is firmly locked to the adjacent vertebral body. Accordingly, both fixation screws 40 and locking pin 50 may be provided with minimal or no allowed toggle. This implant allows either preference.

In the rigidly fixed version, the locking pin 50 may be provided without the contour on its underside (i.e., a relatively flat underside) while the opening 64, 70 of the plate 60 would likewise not include a contour. Thus, when secured together, the locking pin 50 and the plate 60 form a rigidly locked construct. It will be appreciated that, instead of having one superior hole and two inferior holes in the implant as shown in the drawings, the implant may have two superior and one inferior holes, or may be adapted to have two superior holes and two inferior holes. As previously discussed, the implant 10 may be configured with any number of holes without departing from the spirit of the invention.

It will also be appreciated that the angular positioning of the various holes, as described above, allows the present implant 10 to be of a relatively small size and therefore insertable within the intervertebral space in the cervical region, where space is at a premium, while still allowing for the securing of the implant 10 by conventional means. Thus, it will be appreciated that the angular positioning of the holes is important to the effective operation of the implant 10 and the ability to "stack" implants in adjacent multilevel procedures without the securing means interfering with each other, which can be of major significance in some situations. For example, it is contemplated that the holes 24 of the implant 10 may be angularly configured to allow the middle fixation screw 40 to be placed between the lateral fixation screws 40 of an implant 10 and attachment system 30 just below it. The locking plate 60 provides a means for ensuring the security and location of the implant 10 once inserted but may be configured to be reversible so as to allow removal of the fixation screws 40 if a revision is required.

Moreover, while a toggle and a rigidly fixed version of the implant 10 and screws 40 are described, it is understood that a combination of toggling and rigid fixation may be accomplished in a single implant 10 and attachment system 30. For example, it is possible to provide an implant 10 that allows toggling of one or more screws 40, while also allowing rigid fixation of the other of the screws 40.

Other embodiments of the invention will be apparent to those skilled in the art from consideration of the specification and practice of the disclosure provided herein. It is intended that the specification and examples be considered as exemplary only.

What is claimed is:

1. A spinal implant assembly comprising:
    an implantable body having an upper surface, a lower surface, an anterior portion, and a non-expandable posterior portion having a fixed height, wherein the body is configured for insertion between vertebral bodies of a patient's spine,
    wherein an aperture is defined within the posterior portion of the body;
    a fixation element configured to be inserted into the aperture of the body, wherein a space exists between the fixation element and an inner surface of the body defining the aperture when the fixation element is fully inserted into the aperture, which permits a non-zero degree of nutation by the fixation element with respect to the aperture;
    a plate having a complementary fit with the posterior portion of the body and configured to nest against the posterior portion of the body, the plate comprising one or more arms, a first of the one or more arms providing an aperture that aligns with the aperture within the posterior portion of the body to permit access to a head portion of the fixation element, wherein the first of the one or more arms or a second of the one or more arms comprises a separate adjustable arm that is adjustable in height relative to a remainder of the plate; and
    at least one locking element shaped to pass through the aperture of the plate and configured for insertion into, and engagement with, the head portion of the fixation element to secure the plate to the fixation element.

2. The spinal implant assembly of claim 1 wherein the implantable body comprises one or more portals for receiving an imaging marker.

3. The spinal implant assembly of claim 1, wherein the aperture of the body is configured to permit from about 3 degrees to about 8 degrees of nutation by the fixation element.

4. The spinal implant assembly of claim 3, wherein the aperture of the body is configured to permit about 5 degrees of nutation by the fixation element.

5. The spinal implant assembly of claim 1, wherein the head portion of the fixation element is configured to permit a non-zero degree of nutation by the locking element.

6. The spinal implant assembly of claim 1, wherein the head portion of the fixation element is configured to rigidly seat the locking element.

7. The spinal implant assembly of claim 1, wherein aperture of the plate is configured to permit a predetermined amount of nutation by the at least one locking element.

8. The spinal implant assembly of claim 1, wherein the plate is configured to rigidly nest on the head portion of the fixation element.

9. The spinal implant assembly of claim 1, wherein the adjustable arm comprises a locking feature to fix a position of the adjustable arm.

10. The spinal implant assembly of claim 1, wherein the plate comprises a slot and the adjustable arm comprises a knob for insertion into the slot.

11. The spinal implant assembly of claim 1, wherein the locking element comprises a cap, pin or plug.

12. The spinal implant assembly of claim 1, wherein the locking element is configured to sit proud atop the plate.

13. The spinal implant assembly of claim 1, wherein the locking element is configured to seat flush against the plate.

14. A method of treating a patient's spine comprising:
    accessing at least a portion of a patient's spine via a posterior approach;
    inserting an implantable body between vertebral bodies of the patient's spine, wherein the body comprises an upper surface, a lower surface, an anterior portion, and a non-expandable posterior portion having a fixed height, wherein a first aperture is defined within the posterior portion of the body
    inserting a fixation element into the first aperture to attach the body to the vertebral bodies, wherein a space exists between the fixation element and an inner surface of the body defining the first aperture when the fixation element is fully inserted into the first aperture, which permits a non-zero degree of nutation by the fixation element with respect to the first aperture;
    placing a plate onto the body, the plate having a complementary fit with the posterior portion of the body and configured to nest against the posterior portion of the body, the plate comprising one or more arms, a first of the one or more arms providing a second aperture that aligns with the first aperture within the posterior portion of the body to permit access to a head portion of the fixation element, wherein the first of the one or more arms or a second of the one or more arms comprises a separate adjustable arm that is adjustable in height relative to a remainder of the plate, the placement being based on aligning the second aperture over the head portion of the fixation element; and
    inserting at least one locking element through the second aperture into the head portion of the fixation element.

15. The method of claim 14, wherein the first aperture is configured to permit from about 3 degrees to about 8 degrees of nutation by the fixation element.

16. The method of claim 15, further comprising permitting a predetermined amount of toggling of the fixation element based on nutation of the fixation element during subsidence of the spinal implant.

17. The method of claim 14, wherein placing the plate comprises adjusting the adjustable arm of the plate to align the second aperture over the head portion of the fixation element.

18. The method of claim 17, further comprising fixing the adjustable arm after the second aperture is aligned.

19. The method of claim 14, wherein inserting the locking element comprises inserting the locking element into a the head portion of the fixation element.

20. The method of claim 19, wherein the head portion permits a predetermined amount of nutation by the locking element.

* * * * *